United States Patent [19]
Heffner et al.

[11] Patent Number: 4,582,823
[45] Date of Patent: Apr. 15, 1986

[54] METHOD FOR TREATING SCHIZOPHRENIA AND MEDICAMENTS THEREFOR

[75] Inventors: Thomas G. Heffner; Stephen E. Harrigan; Jerry A. Weisbach, all of Ann Arbor, Mich.

[73] Assignee: Warner-Lambert Company, Morris Plains, N.J.

[21] Appl. No.: 640,905

[22] Filed: Aug. 15, 1984

[51] Int. Cl.⁴ .............................................. A61K 31/70
[52] U.S. Cl. ..................................................... 514/46
[58] Field of Search ................ 424/180, 244; 536/26; 514/46

[56] References Cited
U.S. PATENT DOCUMENTS 3,438,991  4/1969  Janssen ................................ 424/244
3,505,451  4/1970  Brunings ............................. 424/244
3,901,876  8/1975  Vorbruggen et al. ................ 536/26
3,978,216  8/1976  Fuxe ..................................... 424/247
4,316,897  2/1982  Lotz ..................................... 424/244

FOREIGN PATENT DOCUMENTS 40325  11/1981  European Pat. Off. ............. 536/26
2406587  8/1975  Fed. Rep. of Germany ........ 536/26

Primary Examiner—Ethel G. Love
Attorney, Agent, or Firm—Joan Thierstein

[57] ABSTRACT

A method for treating schizophrenia without precipitating neurological side effects such as extrapyramidal syndrome and tardive dyskinesia by administering prior to or concomitantly with haloperidol a diphenylalkyladenosine or diphenylalkyl-2-amino-adenosine is described as well as pharmaceutical compositions therefor.

12 Claims, 2 Drawing Figures

METHOD FOR TREATING SCHIZOPHRENIA AND MEDICAMENTS THEREFOR

BACKGROUND OF THE INVENTION

Haloperidol, described in U.S. Pat. No. 3,438,991, is a well-known neuroleptic agent used for treating psychoses, such as schizophrenia. Use of haloperidol causes side effects including acute extrapyramidal syndrome (EPS) which is usually seen soon after antipsychotic therapy is begun as well as the more chronic dystonic syndrome known as tardive dyskinesia which sometimes emerges during long-term antipsychotic use.

Attempts at reducing the side effects of haloperidol have been reported. U.S. Pat. No. 3,978,216 describes the use of a gabergic compound administered prior to or with a neuroleptic agent to reduce tardive dyskinesia. Benzodiazepines have been reported to be effective in the reduction of serum prolactin when used with haloperidol, U.S. Pat. No. 4,316,897. Desipramine and imipramine have been reported to reduce Parkinson-like symptoms in the treatment of schizophrenia with haloperidol in U.S. Pat. No.3,505,451.

The present invention has for its object a method of treating psychoses, e.g., schizophrenia, and reducing the side effects of such treatment, such as acute extrapyramidal syndrome and tardive dyskinesia by administering a novel adenosine derivative prior to or concomitant with haloperidol therapy.

Another object of the present invention is a new pharmaceutical composition comprising effective amounts of haloperidol and a novel adenosine derivative with a carrier to treat schizophrenia with reduced side effects. The presence of the novel adenosine compound not only reduces the chance of tardive dyskinesia but increases the efficacy of haloperidol thereby requiring lower doses of haloperidol in the therapy.

SUMMARY OF THE INVENTION

Accordingly the present invention relates to a pharmaceutical composition for treating schizophrenia without precipitating neurological side effects comprising an effective amount of
(a) a compound of the formula

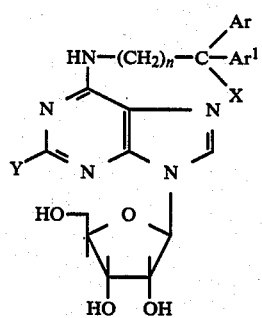

wherein Ar and Ar¹ are each independently phenyl or phenyl substituted by halogen, hydroxy, lower alkoxy or trifluoromethyl; n is 1 or 2; Y is hydrogen or amino, and X is hydrogen, hydroxy or lower alkyl, or a pharmaceutically acceptable acid addition salt thereof, and
(b) an effective amount of haloperidol, together with a pharmaceutically acceptable carrier.

The present invention also relates to a method of treating schizophrenia without precipitating neurological side effects in a subject suffering therefrom comprising administering to said subject (a) a compound of the formula I or a pharmaceutically acceptable acid addition salt thereof prior to or concomitantly with (b) haloperidol in unit dosage form.

DETAILED DESCRIPTION

Figure 1:
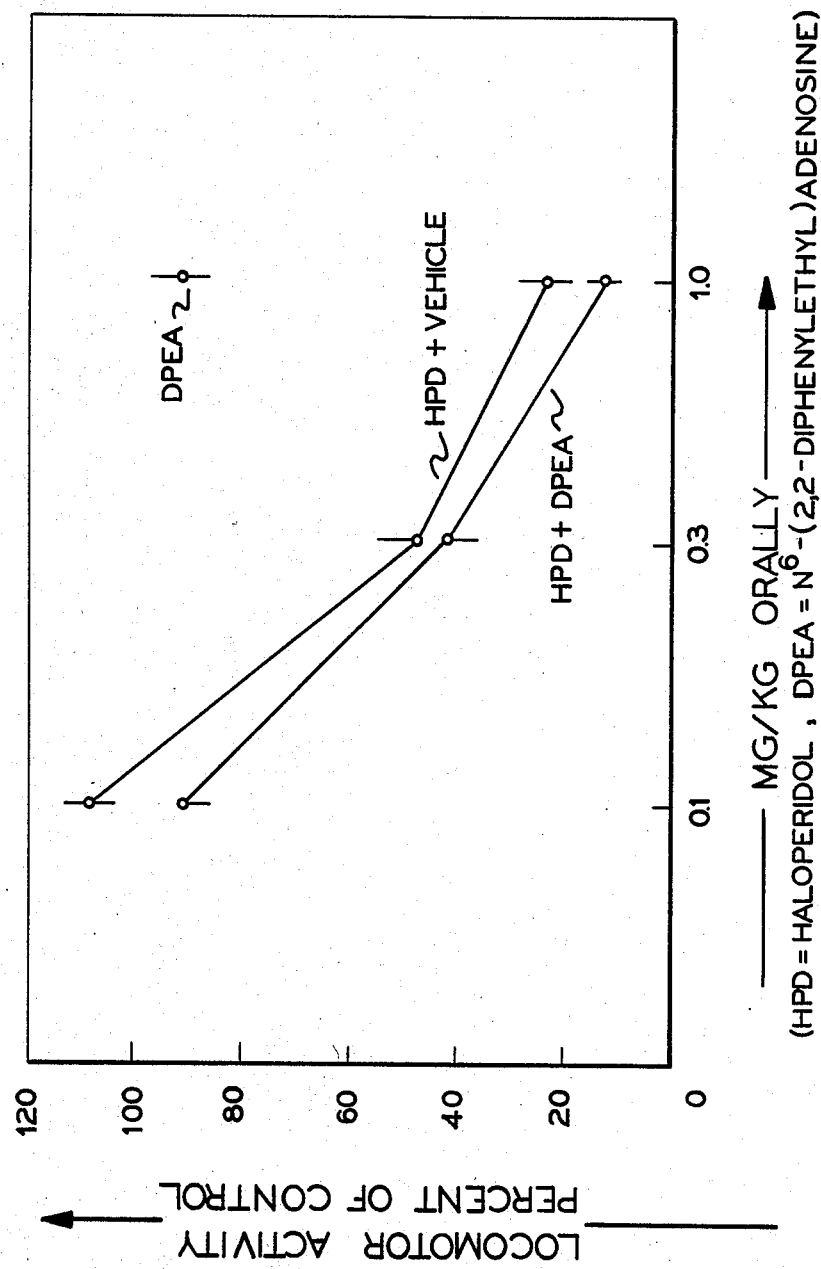

In the compounds of the formula I, the term "lower alkyl" is meant to include a straight or branched alkyl group having from 1 to 6 carbon atoms such as, for example, methyl, ethyl, propyl, isopropyl, butyl, sec-butyl, isobutyl, tertiarybutyl, amyl, isoamyl, neopentyl, hexyl, and the like.

Halogen includes particularly fluorine, chlorine or bromine.

Lower alkoxy is 0-alkyl of from 1 to 6 carbon atoms as defined above for "lower alkyl".

Lower alkanoyloxy is a straight or branched

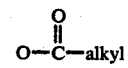

group of from 1 to 6 carbon atoms in the alkyl chain as defined above.

The compounds of formula I are useful both in the free base form and in the form of acid addition salts. Both forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as ethanesulfonic acid, benzenesulfonic acid, p-toluenesulfonic acid, and the like, giving the hydrochloride, sulfamate, ethanesulfonate, benzenesulfonate, p-toluenesulfonate, and the like, respectively.

The acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The compounds of the invention may contain an asymmetric carbon atom at the carbon atom connecting groups A, Ar, Ar¹ and X when Ar and Ar¹ are different. The invention includes the individual enantiomers, the pure S, the pure R isomer, and mixtures thereof including the racemic modification. The individual enantiomers may be prepared or isolated by methods known in the art.

The compounds of formula I may be conveniently synthesized by reacting a 6-halopurine riboside of formula II with the requisite diaryl alkyl amine of formula III in an inert solvent such as alcohol, or an aprotic solvent such as dimethylformamide between about 25° to about 130° C. for from 1–48 hours. It is useful to add a base such as triethylamine, or calcium carbonate to neutralize the hydrogen halide formed as a byproduct of the reaction, but this can also be accomplished by using an extra equivalent of the aryl alkylamine. It is also convenient, although not necessary, to protect the ribofuranose hydroxyl groups as acetate or benzoate esters which can be removed with ammonium hydroxide or sodium methoxide following the synthesis of the $N^6$-substituted adenosine. The reaction is illustrated as follows:

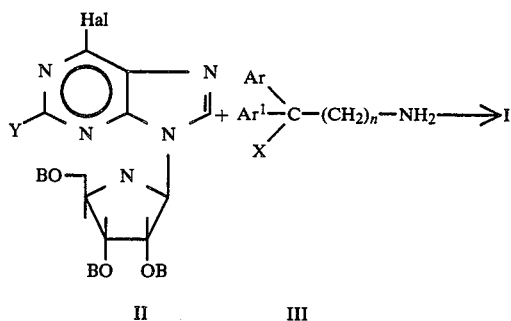

wherein B is H, acetyl or benzoyl; Hal is halogen, preferably chlorine or bromine, and Y, n, Ar, $Ar^1$, and X are as defined for formula I.

In addition, compounds of formula I wherein Y is amino, may also be prepared from 2,6-dichloropurine riboside triacetate of formula IV in a stepwise manner, by first reacting a compound of the formula IV with the requisite diphenyl alkyl amine of formula III to give a compound of formula V, followed by replacing the chlorine atom at $C_2$ with the group Y using nucleophilic displacement conditions, and removing the acetate protecting groups as illustrated below.

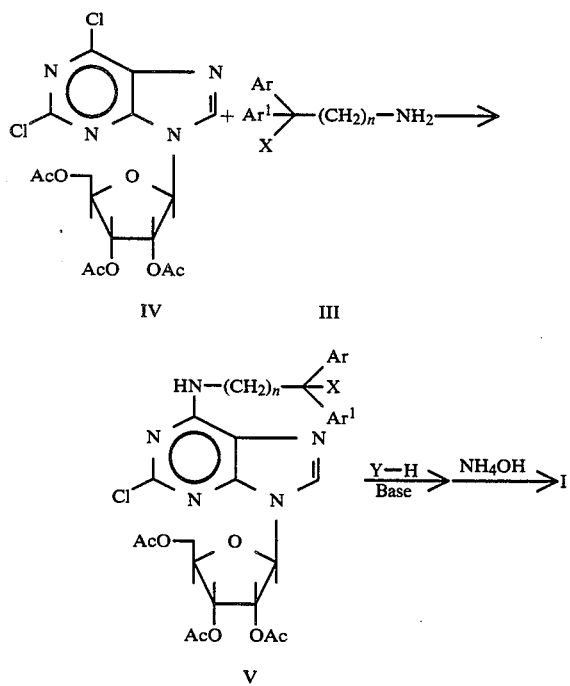

The compounds of formula I have been previously described as having neuroleptic and antihypertensive activity. Particulars relating to pharmacological activity and chemical preparation are reported in U.S. patent application Ser. No. 519,284 of Aug. 1, 1983, now abandoned, for which reference is incorporated therein.

The present invention relates to the discovery that treatment of schizophrenia with haloperidol may be enhanced with lesser neurological side effects by administering prior to or concomitant with haloperidol an effective amount of a compound of the formula I or a pharmaceutically acceptable acid addition salt thereof.

Preferred combinations are those containing haloperidol and a compound of the formula I wherein X is hydrogen and Ar, $Ar^1$, n, and Y are as defined above.

Particularly preferred combinations are those containing haloperidol and $N^6$-(2,2-diphenylethyl)-adenosine and $N^6$-(2,2-diphenylethyl)-2-aminoadenosine.

According to this invention, a combination of a compound of formula I or a pharmaceutically acceptable acid addition salt thereof is administered prior to or concomitantly with haloperidol in an effective amount which comprises a total daily dosage of about 15 to 250 mg, preferably 15 to 150 mg of compound of formula I and about 0.5 to 100 mg, preferably 0.5 to 10 mg of haloperidol to a subject, e.g., a mammalian species, suffering from psychoses, e.g., schizophrenia. Such total daily dosages can be used in a single administration of the total amount or in divided doses 2 to 3 times daily. Generally, a b.i.d. or t.i.d. is preferred. This preferred dosage is about 7.5 to 75 mg of compound of formula I or a pharmaceutically acceptable acid addition salt thereof and about 0.5 to 5 mg of haloperidol 2 times daily or about 7.5 to 75 mg of compound of formula I and about 0.5 to 5 mg of haloperidol 3 times daily. The preferred route of administration is oral.

The present invention further includes a method for treating psychoses, e.g., schizophrenia, in mammals suffering therefrom comprising administering to such mammals either orally or parenterally a corresponding pharmaceutical composition containing a compound of the formula I as defined above and haloperidol in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of active ingredients. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active components (with or without other carriers) are surrounded by carrier, which are thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredients are dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active materials, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of active components. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compounds in a unit dose of preparation may be varied or adjusted from 1 mg to 500 mg preferably to 5 to 100 mg according to the particular application and the potency of the active ingredients.

In therapeutic use as described above, the mammalian dosage range for a 70 kg subject is from 0.1 to 5 mg/kg of body weight per day or preferably 1 to 3 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following Examples further illustrate the invention.

EXAMPLE 1

N$^6$-(2,2-Diphenylethyl)adenosine

A solution of 6-chloro-9-$\beta$-D-ribofuranosyl-purine (11.47 g, 0.04 mol) and 2,2-diphenylethylamine (19.73 g, 0.10 mol, 250 mol%) in absolute ethanol (300 ml) is heated at reflux under nitrogen with magnetic stirring for three days, during which time the starting material is consumed according to TLC analysis (5/1 CHCl$_3$/MeOH). The cooled reaction mixture is evaporated in vacuo to a gummy foam which is dissolved in ethyl acetate. Two crops of crystals are obtained and discarded. The filtrate is diluted with hexane, the resulting oil is separated, and the remainder is evaporated in vacuo to a white foam. Neither the oil nor the foam crystallizes from ethyl acetate/hexane, ethyl acetate alone, or ethanol/water, but crystallization of the combined oil and foam twice from methanol affords N$^6$-(2,2-diphenyl)adenosine as a white solid, mp 106.5°–115° C. (after recrystallization from methanol).

Anal. Calcd. for C$_{24}$H$_{25}$N$_5$O$_4$.0.3H$_2$O: C, 63.64; H, 5.71, N, 15.47, Cl, 0.00, H$_2$O, 1.19. Found: C, 63.97, H, 5.48, N, 15.48, halogen (total), 0.00, H$_2$O (Karl Fisher) 1.44.

EXAMPLE 2

N$^6$-(2,2-Diphenylethyl)-2-aminoadenosine

A mixture of 1.25 g of 6-chloro-2-amino-9-($\beta$-D-ribofuranosyl)purine, 0.899 g of 2,2-diphenylethylamine and 0.503 g of triethylamine is heated under reflux in 30 ml of absolute ethanol under a nitrogen atmosphere for 18 hours. The solvent is evaporated to dryness and residue is treated with 50 ml of cold water. The insoluble organic material is filtered, dried, and purified by medium pressure liquid chromatography on silica gel. The product is eluted with 10% methanol-chloroform. Evaporation of the solvent from the pure fractions affords a colorless solid material. Crystallization from a mixture of CHCl$_3$-2-propanol (10:1) and hexane affords N$^6$-(2,2-diphenylethyl)-2-aminoadenosine, mp 134°–137° C.

Anal. Calcd. for C$_{24}$H$_{26}$N$_6$O$_4$ C, 62.32; H, 5.66; N, 18.17 Found: C, 62.18; H, 5.53; N, 17.88

EXAMPLE 3

| INJECTABLES | |
| --- | --- |
| N$^6$—(2,2-Diphenylethyl)adenosine | 15 mg–150 mg |
| Haloperidol | 0.5 mg–5 mg |
| Water for Injection USP q.s. | |

The above compounds are dissolved in the water and passed through a 0.22 micron filter. Aliquots of the filtered solution are added to ampoules or vials, sealed, and sterilized.

EXAMPLE 4

| SYRUP | |
| --- | --- |
| 200 mg Active ingredients/5 ml syrup | |
| N$^6$—(2,2-Diphenylethyl)adenosine | 2.0 g |
| Haloperidol | 0.2 g |

| -continued | |
|---|---|
| SYRUP | |
| 200 mg Active ingredients/5 ml syrup | |
| Purified Water USP | 200 ml |
| Cherry Syrup q.s. or | 1000 ml |

The above compounds are dissolved in the water and to this solution the syrup is added with mild stirring.

EXAMPLE 5

| CAPSULES | |
|---|---|
| 50 mg, 125 mg or 250 mg | |
| $N^6$—(2,2-Diphenylethyl)adenosine | 250 g |
| Haloperidol | 5 g |
| Lactose USP, Anhydrous q.s. | 250 g |
| Sterotex Powder HM | 5 g |

Combined the above compounds and the Lactose in a Tumble blend for two minutes, blend for one minute with the intensifier bar and then tumble blend again for one minute. A portion of the blend is then mixed with the Sterotex Powder, passed through a #30 screen, and added back to the remainder of the blend. The mixed ingredients are then blended for one minute, blended with the intensifier bar for thirty seconds, and tumble blended for an additional minute. Appropriate sized capsules are filled with 141 mg. 352.5 mg or 705 mg of the blend, respectively, for the 50 mg, 125 mg, and 250 mg containing capsules.

EXAMPLE 6

| TABLETS | |
|---|---|
| 50 mg, 125 mg or 500 mg | |
| $N^6$—(2,2-Diphenylethyl)adenosine | 125 g |
| Haloperidol | 25 g |
| Corn Starch NF | 200 g |
| Cellulose, Microcrystalline | 46.0 g |
| Sterotex Powder HM | 4.0 g |
| Purified Water q.s. | 300.0 ml |

Combined the corn starch, the cellulose, and the above compounds together in a planetary mixer and mix for two minutes. Add the water to this combination and mix for one minute. The resulting mix is spread on trays and dried in a hot air oven at 50° C. until a moisture level of 1 to 2 percent is obtained. The dried mix is then milled with a Fitzmill through a #RH2B screen, and added back to the milled mixture and the total blended for five minutes by drum rolling. Compressed tablets of 150 mg, 375 mg, and 750 mg respectively, of the total mix are formed with appropriate sized punches for the 50 mg, 125 mg, or 500 mg containing tablets.

The usefulness of the pharmaceutical compositions of the present invention is demonstrated by the enhanced neuroleptic activity of the combined active components without precipitating neurological side effects in standard pharmacological test procedures.

EVALUATION OF $N^6$-(2,2-DIPHENYLETHYL)ADENOSINE, A POTENTIAL ANTIPSYCHOTIC, IN COMBINATION WITH HALOPERIDOL IN RAT LOCOMOTOR ACTIVITY AND SCREEN TEST (MAST)

METHODS

Sprague-Dawley male rats were used. $N^6$-(2,2-Diphenylethyl)adenosine was dissolved in Emulphor ® and 0.2% Methocel ®. Haloperidol (HPD) was dissolved in acetic acid, the pH was adjusted to 5.5 with NaOH, and NaOH, and the volume adjusted with 0.2% Methocel ® vehicle. Treatments, dosages, and the number of animals randomly assigned to each treatment combination are shown in Table 1. Haloperidol versus vehicle treatments were included each time the adenosine was tested. Treatments were given orally in volumes of 5 ml/kg one hour before testing was started.

Each animal was given three consecutive trials in the inverted screen test. A score of "0" was given if the rat climbed to the top surface or clung to the inverted screen for 20 seconds. A score of "1" was given if the animal fell off. Scores were summed across animals and trials for each treatment. Treatment scores were expressed as percentage of screen fall-off less the control failures.

Each animal was then placed in a darkened actophotometer and locomotor activity was recorded automatically by a microcomputer for 30 minutes. Locomotor activity data were compared to the mean response of vehicle treated control and were expressed as percentage of activity relative to control.

RESULTS

Figure 2:
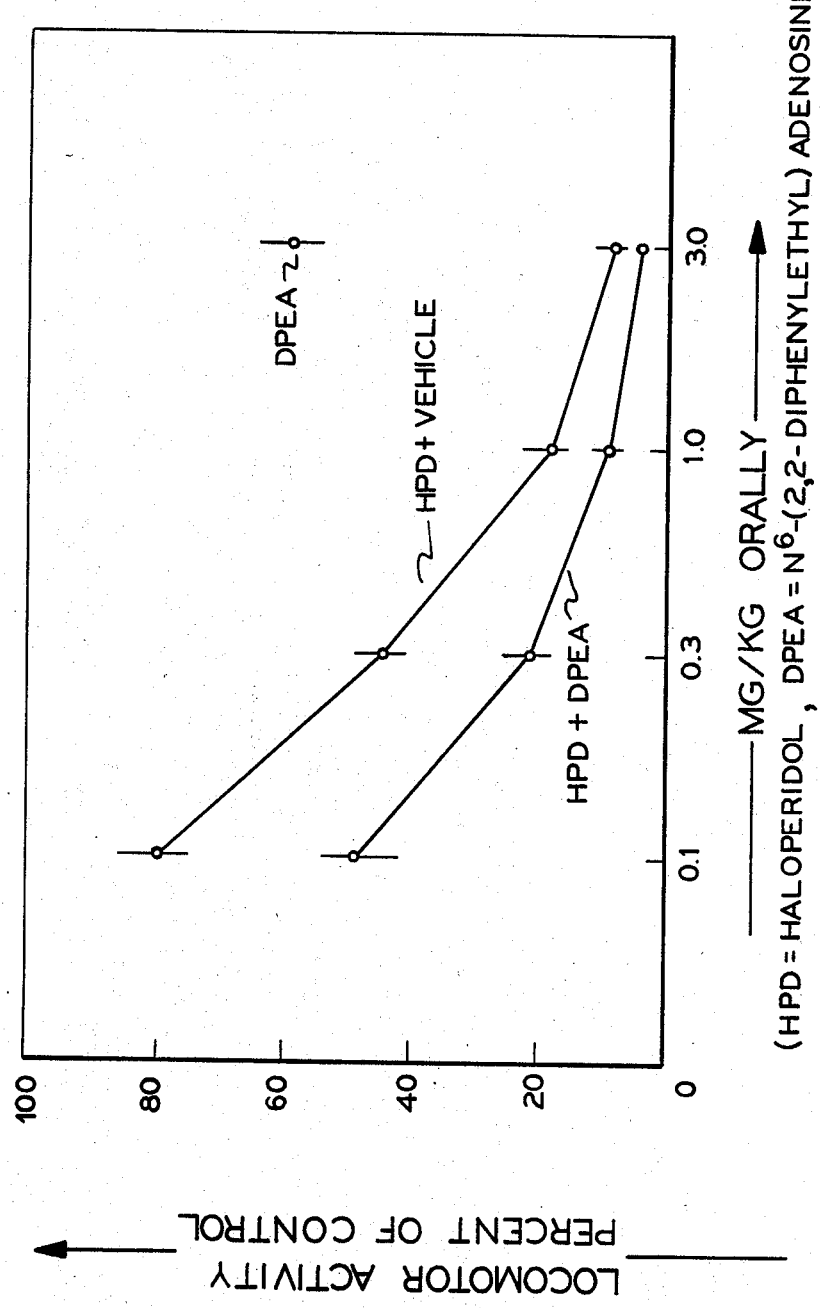

The results are shown in FIGS. 1 and 2 and Table 1. At 1.0 mg/kg, $N^6$-(2,2-diphenylethyl)-adenosine did not significantly alter locomotion and likewise did not significantly alter the dose-related inhibition of spontaneous locomotion caused by haloperidol (FIG. 1). At 3.0 mg/kg, the adenosine alone reduced locomotion by 50% (FIG. 2). The 3.0 mg/kg dose of the adenosine enhanced the locomotor inhibition produced by 0.1 and 0.3 mg/kg of haloperidol (FIG. 2).

The inverted screen results are shown in Table 1. The combination of the haloperidol dose range with $N^6$-(2,2-diphenylethyl)adenosine at either 1 or 3 mg/kg had equivocal results in the inverted screen test.

$N^6$-(2,2-Diphenylethyl)adenosine enhanced haloperidol induced inhibition of rat locomotor activity. The magnitude of response suggests that $N^6$-(2,2-diphenylethyl)adenosine has an additive effect in combination with haloperidol.

TABLE 1

| Effects of $N^6$—(2,2-Diphenylethyl)adenosine and Haloperidol (HPD) in Rat Locomotor Activity and Screen Test | | | | |
|---|---|---|---|---|
| First Treatment Orally 1 Hr Before Test | Second Treatment Orally 1 Hr Before Test | No. Of Animals | Locomotor Activity % Of Control ± SEM* | Inverted Screen Test % Fall Off ± SEM |
| $N^6$—(2,2-Diphenylethyl)adenosine, 1 mg/kg | Vehicle, 5 ml/kg | 9 | 93.8 ± 8.9 | 11.1 ± 11.1 |
| $N^6$—(2,2-Diphenylethyl)adenosine, 1 mg/kg | HPD, 0.1 mg/kg | 9 | 92.0 ± 2.8 | 14.8 ± 8.1 |
| $N^6$—(2,2-Diphenylethyl)adenosine, 1 mg/kg | HPD, 0.3 mg/kg | 9 | 40.7 ± 4.9 | 29.6 ± 11.7 |
| $N^6$—(2,2-Diphenylethyl)adenosine, 1 mg/kg | HPD, 1.0 mg/kg | 9 | 10.8 ± 2.6 | 40.7 ± 12.1 |
| Vehicle, 5 ml/kg | HPD, 0.1 mg/kg | 9 | 108.6 ± 8.6 | 22.2 ± 9.6 |
| Vehicle, 5 ml/kg | HPD, 0.3 mg/kg | 9 | 46.0 ± 7.2 | 11.1 ± 7.8 |

TABLE 1-continued

Effects of $N^6$—(2,2-Diphenylethyl)adenosine and Haloperidol (HPD) in Rat Locomotor Activity and Screen Test

| First Treatment Orally 1 Hr Before Test | Second Treatment Orally 1 Hr Before Test | No. Of Animals | Locomotor Activity % Of Control ± SEM* | Inverted Screen Test % Fall Off ± SEM |
|---|---|---|---|---|
| Vehicle, 5 ml/kg | HPD, 1.0 mg/kg | 9 | 21.8 ± 2.9 | 18.5 ± 8.1 |
| $N^6$—(2,2-Diphenylethyl)adenosine, 3 mg/kg | Vehicle, 5 ml/kg | 17 | 58.7 ± 5.2 | 13.7 ± 6.4 |
| $N^6$—(2,2-Diphenylethyl)adenosine, 3 mg/kg | HPD, 0.1 mg/kg | 8 | 49.1 ± 10.0 | 8.3 ± 5.4 |
| $N^6$—(2,2-Diphenylethyl)adenosine, 3 mg/kg | HPD, 0.3 mg/kg | 17 | 21.6 ± 5.0 | 31.4 ± 8.3 |
| $N^6$—(2,2-Diphenylethyl)adenosine, 3 mg/kg | HPD, 1.0 mg/kg | 17 | 9.8 ± 2.1 | 35.3 ± 7.3 |
| $N^6$—(2,2-Diphenylethyl)adenosine, 3 mg/kg | HPD, 3.0 mg/kg | 9 | 4.3 ± 1.3 | 44.4 ± 13.6 |
| Vehicle, 5 ml/kg | HPD, 0.1 mg/kg | 8 | 80.4 ± 10.2 | 8.3 ± 5.4 |
| Vehicle, 5 ml/kg | HPD, 0.3 mg/kg | 17 | 44.0 ± 4.5 | 21.6 ± 8.1 |
| Vehicle, 5 ml/kg | HPD, 1.0 mg/kg | 17 | 18.0 ± 2.5 | 50.9 ± 5.0 |
| Vehicle, 5 ml/kg | HPD, 3.0 mg/kg | 9 | 8.2 ± 2.1 | 51.8 ± 13.7 |

*SEM = Standard Error of the Mean.

EFFECTS OF $N^6$-(2,2-DIPHENYLETHYL)ADENOSINE, A POTENTIAL ANTIPSYCHOTIC, ON HALOPERIDOL-INDUCED DYSTONIAS IN CEBUS MONKEYS

METHODS

Subjects were adult Cebus monkeys (*Cebus appella*) of either sex that had been sensitized to haloperidol by chronic weekly administration of the drug. At the time of the present study, dystonic reactions were consistently manifest following 0.2 mpk PO haloperidol. These sensitized monkeys serve as a preclinical model of the extrapyramidal syndrome (EPS) and tardive dyskinesia caused by antipsychotic drugs.

On test days, animals were given $N^6$-(2,2-diphenylethyl)adenosine before or after haloperidol. Drugs were prepared as suspensions in 0.2% Methocel for oral and IP injection. Solutions for IM injections of haloperidol were made using lactic acid and of the adenosine using ethanol.

RESULTS $N^6$-(2,2-Diphenylethyl)adenosine administered IP together with haloperidol PO prevented the development of dystonia in a dose dependent fashion with an estimated ED50 of 2.3 mpk (Table II). Similar results were obtained when haloperidol was administered IM 30 minutes after IP of the adenosine. In both cases, the adenosine induced depression prior to the expected time of onset of the effects of haloperidol. Animals displaying dystonia following combined $N^6$-(2,2-diphenylethyl)adenosine and haloperidol treatment also displayed depression; the dystonia in such animals appeared to be less intense than those seen in the absence of the adenosine.

Intramuscular $N^6$-(2,2-diphenylethyl)adenosine (8 mpk) administered after dystonias had been induced by haloperidol (IM or PO) had no effect on the severity of dystonia (Table III). However, additional tests reveal that $N^6$-(2,2-diphenylethyl)adenosine administered IM is less effective in blocking haloperidol-induced dystonia than when administered by other routes. For example, 8 mg/kg IM of $N^6$-(2,2-diphenylethyl)adenosine did not block dystonia induced by haloperidol (0.5 mg/kg PO) in 3/6 animals tested. Because of the severity of haloperidol-induced dystonias in sensitized monkeys, the ability of $N^6$-(2,2-diphenylethyl)adenosine to reverse dystonia when administered by routes other than IM cannot be tested safely.

$N^6$-(2,2-Diphenylethyl)adenosine administered together with haloperidol orally by capsule did not appreciably affect the development or severity of dystonias (Table IV). Haloperidol (0.5 mg/kg in a capsule) alone caused dystonia in 5 of 5 monkeys, whereas haloperidol with the adenosine (5 mg/kg in a capsule) elicited dystonia in 5 of 6 monkeys. However, coadministration of 5 mg/kg PO $N^6$-(2,2-diphenylethyl)adenosine and 0.5 mg/kg haloperidol in a solution by gavage resulted in a marked reduction in the severity of dystonia in 4 of 5 animals tested.

When administered prior to haloperidol, $N^6$-(2,2-diphenylethyl)adenosine prevented the dystonia normally produced by haloperidol in sensitized Cebus monkeys. Although the adenosine did not reverse ongoing dystonia induced by haloperidol when administered IM, this may be related to the reduced ability of the adenosine to block haloperidol-induced dystonia after IM administration. Although combination of the adenosine and haloperidol in the same capsule did not prevent dystonia induced by haloperidol, coadministration of a solution of the two agents by gavage resulted in reduced severity of dystonia.

TABLE II

Blockade of haloperidol-induced dystonia by $N^6$—(2,2-Diphenylethyl)adenosine

| $N^6$—(2,2-Diphenylethyl)adenosine | | | Haloperidol | | | # showing dystonia/ Total |
|---|---|---|---|---|---|---|
| Dose (mpk) | Route | Injection Time | Dose (mpk) | Route | Injection Time | |
| 20 | IP (1) | 0 | 0.5 | PO (2) | 0 (4) | 0/6 |
| 5 | IP | 0 | 0.5 | PO | 0 | 1/6 |
| 1.5 | IP | 0 | 0.5 | PO | 0 | 4/6 |
| 0.5 | IP | 0 | 0.5 | PO | 0 | 5/5 |
| 20 | IP | 0 | 0.05 | IM (3) | +30 Min. (5) | 0/6 |
| 5 | IP | 0 | 0.05 | IM | +30 Min. | 0/6 |

TABLE II-continued

Blockade of haloperidol-induced dystonia by $N^6$—(2,2-Diphenylethyl)adenosine

| $N^6$—(2,2-Diphenylethyl)adenosine | | | Haloperidol | | | # showing dystonia/ |
|---|---|---|---|---|---|---|
| Dose (mpk) | Route | Injection Time | Dose (mpk) | Route | Injection Time | Total |
| 0 | IP | 0 | 0.05 | IM | +30 Min. | 5/5 |

(1) The onset of action (depression) was 5–10 minutes.
(2) The onset of action (dystonia) was 1–3 hours.
(3) The onset of action (dystonia) was 3–7 minutes.
(4) Injected immediately after $N^6$—(2,2-diphenylethyl)adenosine.
(5) Injected 30 minutes after $N^6$—(2,2-diphenylethyl)adenosine.

TABLE III

Attempted Reversal of Haloperidol-induced Dystonia by $N^6$—(2,2-diphenylethyl)adenosine

| $N^6$—(2,2-diphenylethyl)adenosine | | | Haloperidol | | | # Reversed/ |
|---|---|---|---|---|---|---|
| Dose (mpk) | Route | Injection Time | Dose (mk) | Route | Injection Time | Total |
| 8 | IM | +30 Min. (1) | 0.05 | IM | 0 | 0/6 |
| 8 | IM | +90 Min. (2) | 0.5 | PO | 0 | 0/6 |

(1) Given 30 minutes after haloperidol. Dystonia present at the time of injection.
(2) Given 90 minutes after haloperidol. Dystonia present at the time of injection.

TABLE IV

Effect of $N^6$—(2,2-diphenylethyl)adenosine and Haloperidol given Together by Capsule

| $N^6$—(2,2-diphenylethyl)adenosine | | | Haloperidol | | | # showing/ dystonia/ |
|---|---|---|---|---|---|---|
| Dose (mpk) | Route | Injection Time | Dose (mk) | Route | Injection Time | Total |
| 5 | PO Capsule | 0(1) | 0.5 | PO Capsule | 0 | 5/6 |
| — | — | — | 0.5 | PO Capsule | 0 | 5/5 |

(1) $N^6$—(2,2-diphenylethyl)adenosine and haloperidol were mixed together in the capsule.

We claim:

1. A method for treating schizophrenia without precipitating neurological side effects which comprises administering either orally or parenterally to a mammal suffering from schizophrenia about 15 to 250 mg per day of
(a) from 15 to 150 mg of a compound of the formula

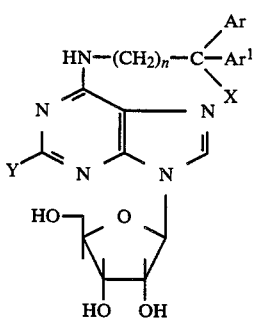

wherein Ar and Ar' are each independently phenyl or phenyl substituted by fluorine, chlorine, or bromine, hydroxy, lower alkoxy of from one to six carbon atoms, or trifluoromethyl; n is one or two; Y is hydrogen or amino, and X is hydrogen, hydroxy or lower alkyl, or a pharmaceutically acceptable acid addition salt thereof, prior to or concomitantly with neurological side effects precipitated by
(b) from 0.5 to 100 mg of haloperidol, together with a pharmaceutically acceptable carrier for oral or parenteral administration.

2. The method of claim 1 wherein the neurological side effect is extrapyramidal syndrome.

3. The method of claim 1 wherein the neurological side effect is tardive dyskinesia.

4. The method of claim 1, wherein (a) is a compound of the formula wherein X is hydrogen.

5. The method of claim 1, wherein (a) is $N^6$-(2,2-diphenylethyl)adenosine.

6. The method of claim 1, wherein (a) is $N^6$-(2,2-diphenylethyl)-2-amino-adenosine.

7. The method of claim 2, wherein (a) is $N^6$-(2,2-diphenylethyl)adenosine.

8. The method of claim 3, wherein (a) is $N^6$-(2,2-diphenylethyl)adenosine.

9. A pharmaceutical composition for treating schizophrenia without precipitating neurological side effects comprising an effective amount of
(a)

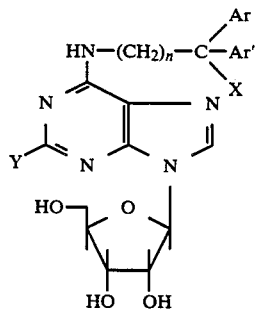

wherein Ar and Ar' are each independently phenyl or phenyl substituted by fluorine, chlorine, or bromine, hydroxy, lower alkoxy of from one to six carbon atoms, or trifluoromethyl; n is one or two; Y is hydrogen or amino, and X is hydrogen, hydroxy or lower alkyl, or a pharmaceutically acceptable acid addition salt thereof, and (b) haloperidol together with a pharmaceutically acceptable carrier for an oral or parenteral unit dosage form of from about 15 to 250 mg having the proportion of (a) to (b) about from 15 mg to 150 mg of (a) to about from 0.5 mg 100 mg of (b).

10. A composition as claimed in claim 9, wherein (a) is a compound of the formula wherein X is hydrogen.

11. A composition as claimed in claim 10, wherein (a) is $N^6$-(2,2-diphenylethyl)adenosine.

12. A composition as claimed in claim 10, wherein (a) is $N^6$-(2,2-diphenylethyl)-2-amino-adenosine.

* * * * *